US010493098B2

(12) United States Patent
Haynes et al.

(10) Patent No.: US 10,493,098 B2
(45) Date of Patent: Dec. 3, 2019

(54) MESOPOROUS SILICA-COATED NANOPARTICLES (71) Applicant: Regents of the University of Minnesota, Minneapolis, MN (US)

(72) Inventors: Christy L. Haynes, Minneapolis, MN (US); Katherine Rose Hurley, Minneapolis, MN (US); Samuel Michael Egger, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 162 days.

(21) Appl. No.: 14/811,490

(22) Filed: Jul. 28, 2015

(65) Prior Publication Data
US 2016/0051471 A1 Feb. 25, 2016

Related U.S. Application Data (60) Provisional application No. 62/030,383, filed on Jul. 29, 2014.

(51) Int. Cl.
A61K 33/26 (2006.01)
A61K 45/06 (2006.01)
A61K 9/00 (2006.01)
A61K 9/51 (2006.01)
C09C 3/06 (2006.01)

(52) U.S. Cl.
CPC ............ *A61K 33/26* (2013.01); *A61K 9/0009* (2013.01); *A61K 9/5115* (2013.01); *A61K 9/5138* (2013.01); *A61K 9/5192* (2013.01); *A61K 45/06* (2013.01); *C01P 2002/72* (2013.01); *C01P 2004/51* (2013.01); *C01P 2004/52* (2013.01); *C01P 2004/64* (2013.01); *C01P 2004/80* (2013.01); *C01P 2004/84* (2013.01); *C01P 2006/14* (2013.01); *C01P 2006/16* (2013.01); *C09C 3/063* (2013.01)

(58) Field of Classification Search
None
See application file for complete search history.

(56) References Cited

U.S. PATENT DOCUMENTS

2010/0056366 A1* 3/2010 Lee .................. B01J 21/063
502/300

OTHER PUBLICATIONS

Al Shamsi, et al., "Biocompatibility of calcined mesoporous silica particles with cellular bioenergetics in murine tissues", Chem Res Toxicol, 23 (11), 1796-1805 (2010).
Borm, et al., "Research strategies for safety evaluation of nanomaterials, part V: role of dissolution in biological fate and effects of nanoscale particles", Toxicol Sci 90 (1), 23-32 (2006).
(Continued)

*Primary Examiner* — Bethany P Barham
*Assistant Examiner* — Barbara S Frazier
(74) *Attorney, Agent, or Firm* — Viksnins Harris Padys Malen LLP (57) ABSTRACT

The present invention relates to mesoporous silica coated nanoparticles comprising a metal oxide nanoparticle core; and a mesoporous silica shell encapsulating metal oxide core; wherein said mesoporous silica shell and the metal oxide core are not in full contact. The nanoparticles of the invention are useful as diagnostic and therapeutic agents.

31 Claims, 11 Drawing Sheets

(56) References Cited

OTHER PUBLICATIONS

Chen, et al., "Maximizing hysteretic losses in magnetic ferrite nanoparticles via model-driven synthesis and materials optimization", ACS Nano 7 (10), 8990-9000 (2013).
Etheridge, et al., "Accounting for biological aggregation in heating and imaging of magnetic nanoparticles", Technology 2 (3), 214-228 (2014).
Etheridge, et al., "Optimizing magnetic nanoparticle based thermal therapies within the physical limits of heating", Ann Biomed Eng 41 (1), 78-88 (2013).
Finnie, et al., "Biodegradability of sol-gel silica microparticles for drug delivery", J Sol-Gel Sci Technol 49, 12-18 (2009).
Guardia, et al., "Water-soluble iron oxide nanocubes with high values of specific absorption rate for cancer cell hyperthermia treatment", ACS Nano 6 (4), 3080-3091 (2012).
He, et al., "In vivo biodistribution and urinary excretion of mesoporous silica nanoparticles: effects of particle size and PEGylation", Small vol. 7 (2), 271-280 (2011).
Hurley, et al., "Effects of Mesoporous Silica Coating and Post-Synthetic Treatment on the Transverse Relaxivity of Iron Oxide Nanoparticles", Chem Mater 25 (9), 1968-1978 (2013).
Hurley, et al., "Effects of Mesoporous Silica Coating on the Transverse Relaxivity of Iron Oxide Nanoparticles", Cancer Nanotechnology Conference: Mechanisms in Nanoparticle Hyperthermia, 20 pages (Dec. 1, 2012).
Hurley, et al., "Synthetic Considerations for Optimal Magnetic Resonance Imaging Contrast in Fe3O4@Mesoporous Silica Nanoparticles", 243rd American Chemical Society National Meeting and Exposition, 1 page (Mar. 27, 2012).
Hurley, et al., "Synthetic Considerations for Optimal MRI Contrast in Magnetic Mesoporous Silica Nanoparticles", 4th EuCheMS Chemistry Congress in Prague, Czech Republic, 1 page (Aug. 22, 2012).
Kim, et al., "Multifunctional uniform nanoparticles composed of a magnetite nanocrystal core and a mesoporous silica shell for magnetic resonance and fluorescence imaging and for drug delivery", Angew Chem Int Ed Engl, 47 (44), 8438-8441 (2008).
Lee, et al. "Intracellular pH-responsive mesoporous silica nanoparticles for the controlled release of anticancer chemotherapeutics", Angew Chem Int Ed Engl, 49 (44), 8214-8219 (2010).
Lee, et al., "Near-Infrared Mesoporous Silica Nanoparticles for Optical Imaging: Characterization and InVivo Biodistribution", Adv Funct. Mater. 19, 215-222 (2009).
Lin, et al., "Multifunctional Composite Nanoparticles: Magnetic, Luminescent, and Mesoporous", Chem Mater 18 (22), 5170-5172 (2006).
Lin, et al., "Stability of small mesoporous silica nanoparticles in biological media", Chem Commun (Camb), 47 (1), 532-534 (2011).
Lin, et al., "Synthesis and Characterization of Biocompatible and Size-Tunable Multifunctional Porous Silica Nanoparticles", Chem Mater 21 (17), 3979-3986 (2009).
Lin, et al., "Ultrastable, Redispersible, Small and Highly Organomodified Mesoporous Silica Nanotherapeutics", Journal of the American Chemical Society, 133, 20444-20457 (2011).
Liong et al., "Multifunctional inorganic nanoparticles for imaging, targeting, and drug delivery", ACS Nano vol. 2 (5), 889-896 (2008).
Liu, et al., "Single and repeated dose toxicity of mesoporous hollow silica nanoparticles in intravenously exposed mice", Biomaterials 32 (6), 1657-1668 (2011).
Lu, et al., "Biocompatibility, biodistribution, and drug-delivery efficiency of mesoporous silica nanoparticles for cancer therapy in animals", Small, 6 (16), 1794-1805 (2010).
Lu, et al., "Mesoporous silica nanoparticles as a delivery system for hydrophobic anticancer drugs", Small vol. 3 (8), 1341-1346 (2007).
Martinez-Boubeta, et al., "Learning from nature to improve the heat generation of iron-oxide nanoparticles for magnetic hyperthermia applications", Sci Rep 3, 1652, 8 pages (2013).
Meng, et al., "Autonomous in vitro anticancer drug release from mesoporous silica nanoparticles by pH-sensitive nanovalves", J. Am. Chem. Soc. 132 (36), 12690-12697 (2010).
Meng, et al., "Engineered design of mesoporous silica nanoparticles to deliver doxorubicin and P-glycoprotein siRNA to overcome drug resistance in a cancer cell line", ACS Nano 4 (8), 4539-4550 (2010).
Nguyen, et al., "Construction of a pH-driven supramolecular nanovalve", Org Lett 8 (15), 3363-3366 (2006).
Radu, et al., "A polyamidoamine dendrimer-capped mesoporous silica nanosphere-based gene transfection reagent", J Am Chem Soc 126 (41), 13216-13217 (2004).
Rosenholm, et al., "Targeting of porous hybrid silica nanoparticles to cancer cells", ACS Nano 3 (1), 197-206 (2009).
Slowing, et al., "Mesoporous silica nanoparticles as controlled release drug delivery and gene transfection carvers", Adv Drug Deliv Rev, 60(11), 1278-1288 (2008).
Slowing, et al., "Mesoporous Silica Nanoparticles for Intracellular Delivery of Membrane-Impermeable Proteins", J Am chem Soc 129 (28), 8845-8849 (2007).
Smolensky, et al., "Fe3O4@organic@Au: core-shell nanocomposites with high saturation magnetisation as magnetoplasmonic MRI contrast agents", Chem Commun (Camb)., 47 (7), 2149-2151 (2011).
Vallet-Regi, et al., "Mesoporous materials for drug delivery", Angew Chem Int Ed Engl, 46 (40), 7548-7558 (2007).
Vivero-Escoto, et al., "Photoinduced intracellular controlled release drug delivery in human cells by gold-capped mesoporous silica nanosphere", J Am Chem Soc., 131 (10), 3462-3463 (2009).
Xia, et al., "Polyethyleneimine coating enhances the cellular uptake of mesoporous silica nanoparticles and allows safe delivery of siRNA and DNA constructs", ACS Nano 3 (10), 3273-3286 (2009).

* cited by examiner

MESOPOROUS SILICA-COATED NANOPARTICLES

PRIORITY

This application claims priority from U.S. Provisional Application Ser. No. 62/030,383 filed Jul. 29, 2014, the disclosure of which is incorporated herein by reference in its entirety.

BACKGROUND

Nanoparticles are being widely investigated for bio-medical applications. The possibility to manipulate and control magnetic properties of magnetic nanoparticles leads to diverse applications in diagnosis, disease treatment and even disease detection. As more and more uses of nanoparticles for in-vivo applications emerge, concerns on their toxicity are raised.

Biodegradable nanoparticles will find use for imaging, cell tracking, drug delivery, cancer therapy et al. A few attempts at making biodegradable nanoparticles are reported, for instance, luminescent porous silica particles in micrometer size. Composite particles made of 4-5 nm Au nanoparticles are also considered biodegradable since they decompose into small clusters that then get cleared out from the body. Although iron oxide magnetic nanoparticles are sometimes considered degradable, evidence for this is not fully established. In addition, the residence time of iron oxide nanoparticles inside the body is long.

There has been burgeoning interest in magnetic hyperthermia because of its potential in cancer treatment with minimized side effects. Under high frequency, targeted, AC magnetic field excitation, heat released from magnetic nanoparticles would lead to degradation of malignant cells. With a large number of heat sources spreading around the targeted area, working efficiency is expected to be high. In this circumstance, precise control of temperature in the safe working range is a challenge. How localized the heat profile can be and how accurate a device can sense in-vivo temperature and control on/off performance are challenges for magnetic hyperthermia.

Interest in materials for self-regulated magnetic hyperthermia is emerging. The goal is to use the ferromagnetic transition temperature to achieve self-regulation. Magnetic materials with Curie temperature close to the safe working range of 42° C.-49° C. have been investigated, including Ni doped Cu, $La_{1-x}Sr_xMnO_3$, Fe—Ni based alloy and Zn ferrite. Although the materials have suitable Curie temperature, most of them have low saturation magnetization, which affects heating efficiency greatly. There are also concerns of the biocompatibility of these materials.

Mesoporous silica nanoparticles (MSNP) are a multifunctional delivery platform that has been shown at cellular and in vivo levels to be capable of delivering drugs such as chemotherapeutic agents and DNA/siRNA to a variety of cancer cell types (Lu et al., Small, vol. 3, pp. 1341-1346, 2007; He et al., Small, vol. 7, pp. 271-280, 2011; Lee et al., Adv. Funct. Mater., vol. 19, pp. 215-222, 2009; Liong et al., ACS Nano, vol. 2, pp. 889-896, 2008; Meng et al., ACS Nano, vol. 4, pp. 4539-4550, 2010; Meng et al., J. Am. Chem. Soc., vol. 132, pp. 12690-12697, 2010; Xia et al., ACS Nano, vol. 3, pp. 3273-3286, 2009; Radu et al., J. Am. Chem. Soc., vol. 126, pp. 13216-13217, 2004; Slowing et al., J. Am. Chem. Soc., vol. 129, pp. 8845-8849, 2007). This delivery platform allows effective and protective packaging of hydrophobic and charged anticancer drugs for controlled and on demand delivery, with the additional capability to also image the delivery site (Liong et al., ACS Nano, vol. 2, pp. 889-896, 2008). The key challenge now is to optimize the design features for efficient and safe in vivo drug delivery (He et al., Small, vol. 7, pp. 271-280, 2011; Lee et al., Angew. Chem. Int. Ed., vol. 49, pp. 8214-8219, 2010; Liu et al., Biomaterials, vol. 32, pp. 1657-1668, 2011; Al Shamsi et al., Chem. Res. Toxicol., vol. 23, pp. 1796-1805, 2010), which can be assessed through the use of human xenograft tumors in nude mice (Lu et al., Small, vol. 6, pp. 1794-1805, 2010).

Based on properties such as large surface area and porous channels that can be used to encapsulate molecules, mesoporous silica nanoparticles (MSNP) have emerged as an efficient drug delivery platform (Kim et al., Angew. Chem., Int. Ed., vol. 47, pp. 8438-8441, 2008; Liong et al., ACS Nano, vol. 2, pp. 889-896, 2008; Lu et al., Small, vol. 3, pp. 1341-1346, 2007; Slowing et al., Adv. Drug Delivery Rev., vol. 60, pp. 1278-1288, 2008; Vallet-Regi et al., Angew. Chem., Int. Ed., vol. 46, pp. 7548-7558, 2007). In addition to the well-developed surface chemistry, silica materials are known to be safe, biodegradable and potentially biocompatible (Borm et al., Toxicol. Sci., vol. 90, pp. 23-32, 2006; Finnie et al., J. Sol-Gel. Sci. Techn., vol. 49, pp. 12-18, 2009). This drug transport system is suitable for the delivery of anticancer drugs, including camptothecin, paclitaxel, and doxorubicin (Kim et al., Angew. Chem., Int. Ed., vol. 47, pp. 8438-8441, 2008; Liong et al., ACS Nano, vol. 2, pp. 889-896, 2008; Vivero-Escoto et al., J. Am. Chem. Soc., vol. 131, pp. 3462-3463, 2009). The chemical stability of the particles contribute to their therapeutic utility by allowing the attachment of functional groups for imaging and targeting applications along with the placement of a series of nanovalves for on-demand drug release (Liong et al., ACS Nano, vol. 2, pp. 889-896, 2008; Nguyen et al., Org. Lett., vol. 8, pp. 3363-3366, 2006; Rosenholm et al., ACS Nano, vol. 3, pp. 197-206, 2009).

SUMMARY

In an aspect of the invention there is provided a mesoporous silica-coated metal oxide nanoparticle comprising a metal oxide nanoparticle core; a layer of a capping agent encompassing the surface of said metal oxide nanoparticle core; and a shell of mesoporous silica encapsulating the nanoparticle; wherein said mesoporous silica layer and the metal oxide core are not in direct contact.

In an aspect of the invention there is provided a mesoporous silica-coated metal oxide nanoparticle comprising: a metal oxide nanoparticle core; and a mesoporous silica shell encapsulating the metal oxide core; wherein the mesoporous silica shell and the metal oxide core are not in full contact.

In another aspect of the invention, there is provided a mesoporous silica coated metal oxide nanoparticle comprising a metal oxide nanoparticle core; a layer of a capping agent encompassing the surface of said metal oxide nanoparticle core; and a layer of mesoporous silica bound to the capping agent; wherein there is a gap between the mesoporous silica layer and the metal oxide core.

In another aspect of the invention, there is provided a process for making a mesoporous silica coated metal oxide nanoparticle comprising:
  i. providing a metal oxide nanoparticle core;
  ii. coating said metal oxide core with a capping agent;
  iii. contacting the coated nanoparticle with a cationic surfactant; and iv. encapsulating said nanoparticle from step (iii) with mesoporous silica shell.

In an aspect of the invention, mesoporous silica coated nanoparticles of the invention are administered to a mammal and heated by subjecting them to an alternating magnetic field. In another aspect, there is provided a method of treating a disease or disorder comprising administering to a mammal a nanoparticle of the invention in which said nanoparticle has bound thereto a drug for treating said disease or disorder.

In another aspect of the invention, there is provided a method of treating a disease or disorder by administering to a mammal a nanoparticle of the invention in which the silica shell is impregnated with a drug for treating said disease or disorder.

In another aspect of the invention there is provided pharmaceutical compositions comprising mesoporous silica-coated nanoparticles of the invention and a pharmaceutically acceptable carrier, excipient or diluent.

DETAILED DESCRIPTION

Figure 1:
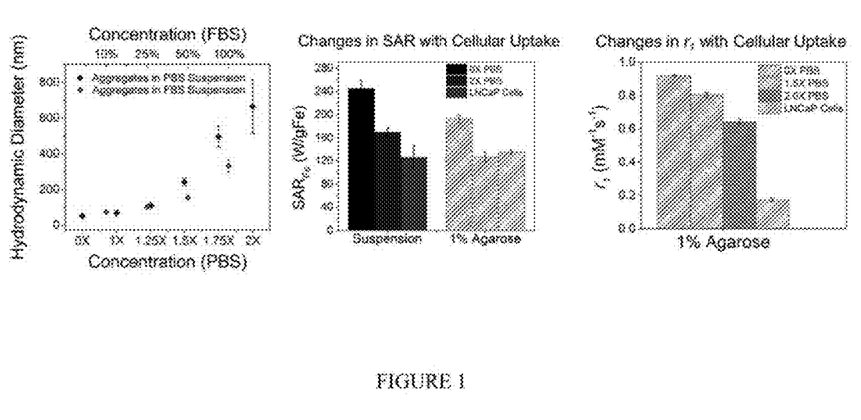
FIG. 1 EMG-308 aggregation and subsequent drop in performance. (Left) controlled exposure to fetal bovine serum (FBS) or phosphate buffered saline (PBS) contributed to reproducible aggregation patterns as measured by dynamic light scattering. (Center) In water suspensions or 1% agarose suspensions, the SAR of EMG-308 was observed to decrease with aggregation (2×PBS) and with cellular uptake (LNCaP cells). (Right) Longitudinal relaxivity ($r_1$) dropped with similar levels of aggregation and exposure to cells.

In recent years, nanoparticles have been touted for their potential use as theranostic (diagnostic and therapeutic) tools in the treatment of cancer. Iron oxide nanoparticles (IONPs) in particular have garnered interest due to their inherent magnetic resonance (MR) contrast and their ability to generate heat upon exposure to an alternating magnetic field (AMF). Unfortunately, the great potential of IONPs has been limited by several factors. Commercially available and clinically-utilized Micromod particles (MagForce) require high field strengths (above the clinically recommended range) to produce an optimum amount of heat (Etheridge, M. L., Bischof, J. C. *Annals of biomedical engineering,* 2013, 41, 78-88). Traditional syntheses of IONPs via thermal decomposition often yield a particle that contains a paramagnetic core, rendering a portion of its mass useless as a contrast or heat-generating agent (Chen, R., et al., *ACS Nano,* 2013, 7, 8990-9000). Theory predicts that the highest heating particles (sizes>15 nm, faceted) are also those which are the hardest to make in bulk due to high temperatures and stringent synthetic conditions (Martinez-Boubeta, et al. *Scientific Reports,* 2013, 3; and Guardia, P., et al., *ACS Nano* 2012, 6, 3080-3091). One candidate, a commercially available IONP from Ferrotec Corporation (Bedord, N.H.) called EMG-308, has been shown to heat very well under clinically relevant field strengths and frequencies as well as providing sufficient MRI contrast (Etheridge, M. L., Bischof, J. C. *Annals of biomedical engineering,* 2013, 41, 78-88). However, the advantages of this particle are substantially diminished when placed in biological suspensions due to inevitable aggregation (FIG. 1) (Etheridge, M. L., et al., *Technology* 2014. *Accepted*).

To harness the potential of IONPs, such as EMG-308, for clinical application, aggregation must be controlled. Mesoporous silica coating has been shown to provide a host of benefits, chief among them being resistance to biological aggregation (colloidal stability) (Lin, Y.-S., et al., *J. Am. Chem. Soc.* 2011, 133, 20444-20457; Lin, Y.-S., et al., *Chem. Commun.* 2011, 47, 532-534). The coating also provides protection from degradation (due to oxidation and dissolution), the ability to be readily functionalized, and the surface area and pore volume to hold large amounts of cargo (Hurley, K. R., et al., *Chem. Mater.* 2013, 25, 1968-1978). It has now been discovered that the inclusion of a functionalized mesoporous silica coating on IONPs, such as EMG-308, results in long term colloidal stability in biological environments, protection from IONP degradation, and cargo loading ability without greatly compromising their heating and imaging capacity. This platform particle makes the high performance IONPs biologically relevant, opening up options for truly effective hyperthermia treatment as an adjuvant to chemo- or radiation therapy.

Figure 2:
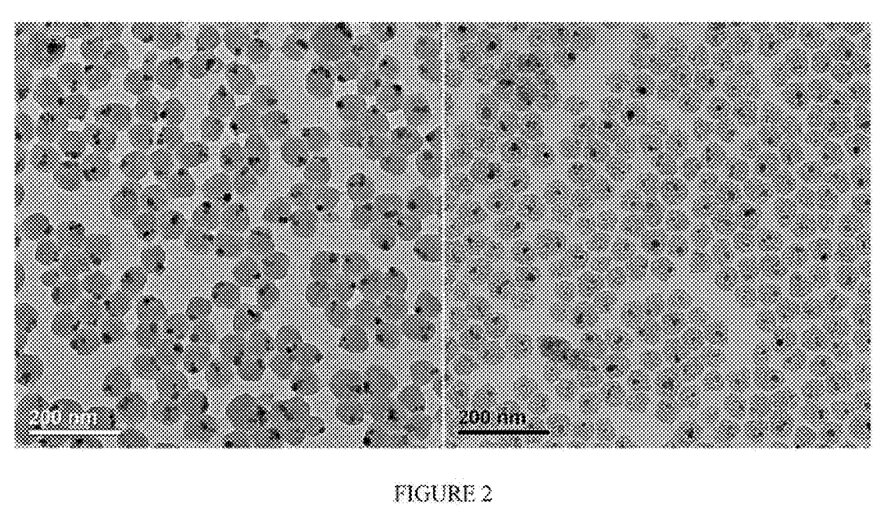
FIG. 2 TEM comparison of morphology of IONPs from example 1 without (left) and with (right) PVP. The additional PVP helps to stabilize the IONPs before coating, leading to fewer cores per particle. It also helps to localize CTAB near the IONPs, contributing to more centered core/shell structures.
Figure 3:
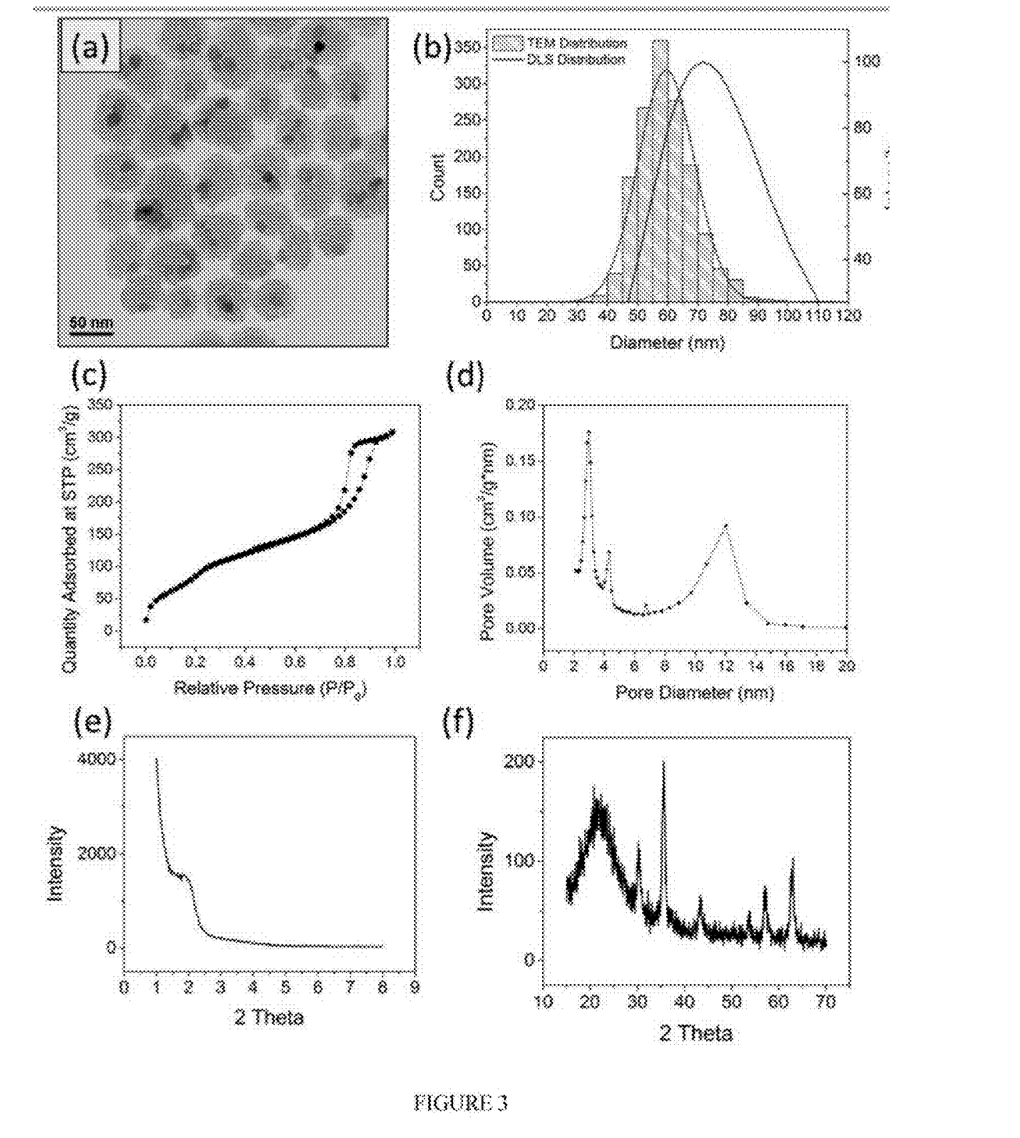
FIG. 3 Materials Characterization of IONPs from example 1. a) TEM images reveal relatively monodisperse particles with hexagonal pore ordering of the silica shell and 1-2 IONP cores per particle. b) TEM and DLS size distributions are narrow and agree with one another. c) Nitrogen physisorption displays a typical type IV isotherm indicative of mesopores. d) BJH pore volume calculations show primary pore sizes of about 2 nm with some larger voids at >10 nm. These are likely indicative of interparticle spacings, not pores within individual particles. e-f) XRD displays characteristic peaks for ordered hexagonal pores, amorphous silica, and $Fe_3O_4$.

Standard particle characterization can be found in FIG. 2. Transmission electron microscopy reveals relatively monodisperse particles with 1-2 cores per particle and an average diameter of 60±2 nm. DLS agrees well, measuring 74±2 nm as the hydrodynamic diameter. Nitrogen physisorption measurements show an overall surface area of 324 $m^2/g$ and a pore volume of 0.48 $cm^3/g$. Although low when compared to bare mesoporous silica nanoparticles, these values are reasonable when taking into account the inclusion of an IONP core and the extensive surface functionalization. X-ray diffraction shows a broad peak near 2 degrees 2θ, indicative of mesopores in a somewhat disordered hexagonal array. Peaks at higher angles can be indexed to $Fe_3O_4$ in agreement with the XRD pattern of the bare IONPs.

In an aspect of the invention, there is provided a mesoporous silica coated metal oxide nanoparticle comprising a metal oxide nanoparticle core; a layer of a capping agent encompassing the surface of said metal oxide nanoparticle core; and a shell of mesoporous silica encapsulating the nanoparticle; wherein said mesoporous silica layer and the metal oxide core are not in direct contact.

In another aspect of the invention, there is provided a mesoporous silica coated metal oxide nanoparticle comprising a metal oxide nanoparticle core; a layer of a capping agent encompassing the surface of said metal oxide nanoparticle core; and a layer of mesoporous silica bound to the capping agent; wherein there is a gap between the mesoporous silica layer and the metal oxide core.

In an embodiment, said metal nanoparticle core is iron-oxide, zero-valent iron, copper, a lanthanide oxide, gold, silver or tin. In an embodiment, said metal nanoparticle core is gold. In an embodiment, said metal nanoparticle core is silver. In an embodiment, said metal nanoparticle core is iron-oxide. In an embodiment, said metal nanoparticle core is zero-valent iron.

In an embodiment, said metal nanoparticle core is copper. In an embodiment, said metal nanoparticle core is a lanthanide oxide. In an embodiment, said capping agent is PVP, PAA (polyacrylamide), PAH (polyalkylamine hydrochloride), PEI (polyethyleneimine) or dextran. In an embodiment, said capping agent is PVP-10. In an embodiment, said capping agent is dextran.

In an embodiment, said capping agent is PEI (polyethyleneimine). The foregoing capping agents are available in various molecular weights and may be in linear or branched forms.

In an embodiment, the silica shell is substantially separated from the metal oxide core. In an embodiment, there is no direct contact between the silica shell and the metal oxide core.

Figure 10:
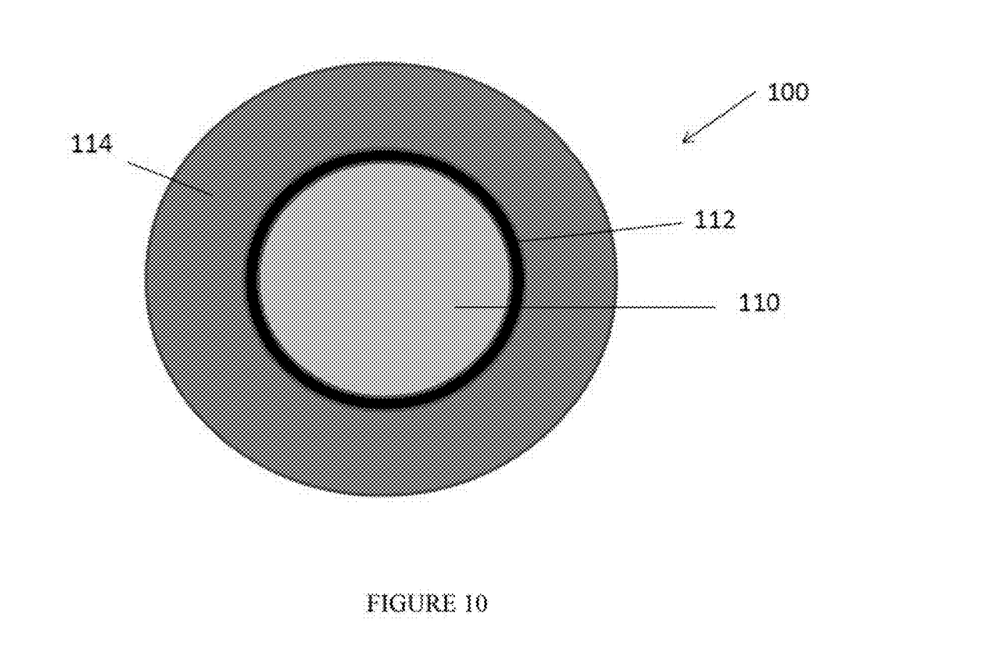
FIG. 10 Illustrates a cross-section of a mesoporous silica coated metal oxide nanoparticle according to one or more embodiments.

Referring to FIG. 10, in one or more embodiments, a mesoporous silica coated metal oxide nanoparticle 100 includes a metal oxide nanoparticle core 110, and a layer of a capping agent 112 encompasses a surface of the metal oxide nanoparticle core 110. In one or more embodiments, the nanoparticle 100 includes a mesoporous silica shell 114 encapsulates metal oxide core 110. In one or more embodiments, the mesoporous silica shell 114 and the metal oxide core 110 are not in direct contact with each other.

Figure 11A:
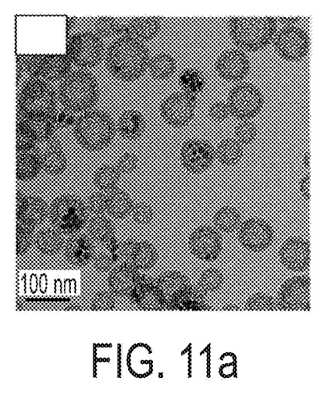
FIGS. 11(a) and 11(b) illustrate images of nanoparticles with open structure according to one or more embodiments.
Figure 11B:
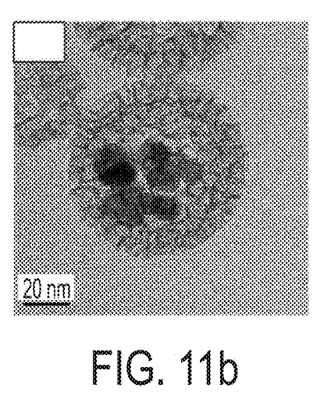

FIGS. 11(a) and 11(b) relate to TEM images of a coated EMG-308 with Open Structure. Such particles can have a mesoporous silica shell encapsulating one or more metal oxide cores without an intervening layer of capping agent. Accordingly, the metal core(s) are typically loose within the mesoporous silica shell. The TEM images show mesoporous silica nanoparticles with an open, lacey structure often encompassing multiple EMG-308 iron oxide nanoparticles.

Figure 6:
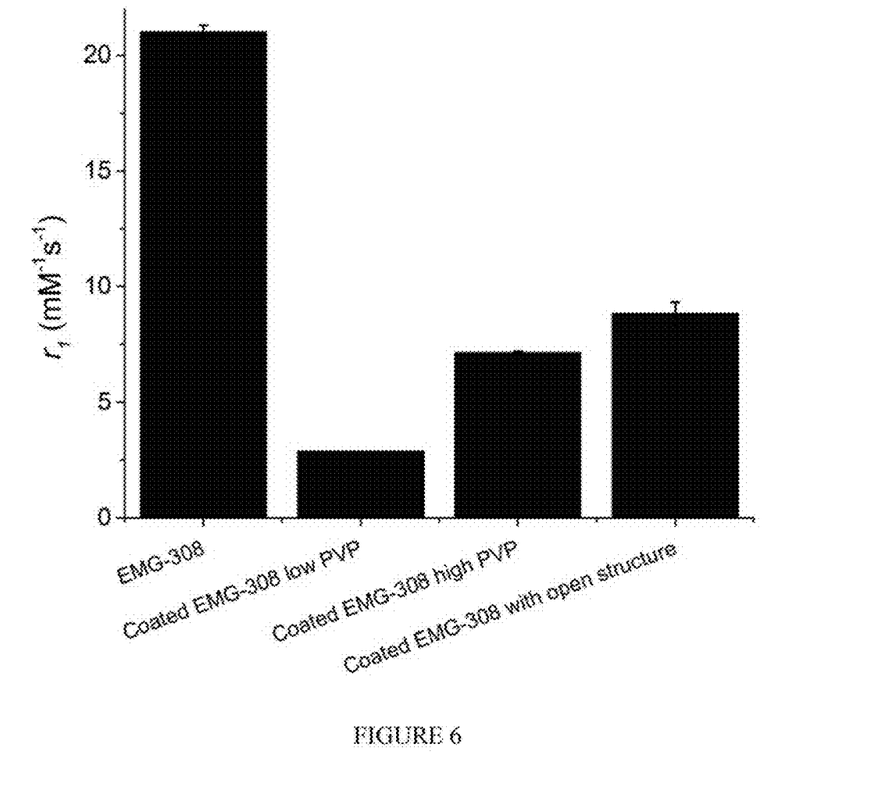
FIG. 6 Effect of 'gap' on longitudinal relaxivity. Coating with mesoporous silica causes a drop in longitudinal relaxivity ($r_1$) which can be partially recovered depending on the relative space between the IONP core and the silica shell. 'Coated EMG-308 with open structure' is a highly porous rattle structure.
Figure 11C:
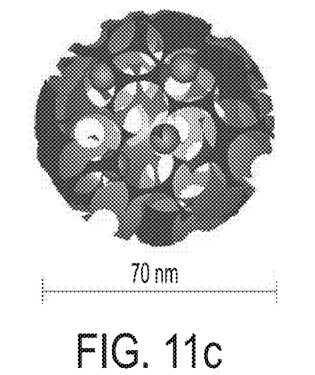
FIG. 11(c) illustrates a diagram of nanoparticles with lacey structure according to one or more embodiments.

FIG. 11(c) illustrates a diagram of the lacey structure of representative nanoparticles, averaging 70 nm in diameter. It should be noted that relaxivity measurements as in FIG. 6 are based on total iron content. Therefore, open structures that contain no iron oxide nanoparticles would not be taken into consideration and the relaxivity values are still readily comparable between nanoparticle types.

In an embodiment, the average distance between the silica shell and the metal oxide core is about 0.1 nm to about 5 nm. In an embodiment, the gap between the silica shell and the metal oxide core is about 0.5 to about 3 nm. In an embodiment, the gap between the silica shell and the metal oxide core is about 2 nm.

In an embodiment, the average hydrodynamic diameter of nanoparticles is about 10 nm to about 300 nm. In an embodiment, the average hydrodynamic diameter of nanoparticles is about 25 nm to about 200 nm. In an embodiment, the average hydrodynamic diameter of nanoparticles is about 100 nm.

In an embodiment, said mesoporous silica coating comprises less than about 50% of mono- or di-OH silanol groups relative to fully condensed. In an embodiment, said mesoporous silica coating comprises less than about 25% of mono- or di-OH silanol groups relative to fully condensed. In an embodiment, said mesoporous silica coating comprises no more than about 10% of mono- or di-OH silanol groups relative to fully condensed.

The surface functionalization of the condensed particle has been utilized previously in our group to enhance colloidal stability. The incorporation of polyethylene glycol, chlorotrimethyl silane or trifluoropropyldimethylchlorosilane, and a hydrothermal treatment all contribute to high surface coverage and more complete condensation of dangling silanol bonds, both of which prevent particle-particle interactions and subsequent aggregation (Lin, Y.-S., et al., *J. Am. Chem. Soc.* 2011, 133, 20444-20457).

Further options include functionalizing the nanoparticles of the invention with at least one of specific targeting groups for cells or tissues, or specific molecules or combinations for in-vivo medical devices. In a further option, the method further includes at least one of imaging with the nanoparticles, controlling the nanoparticles with a magnetic heating process to release molecules and to degrade the particles, sorting the nanoparticles. Accordingly, in an embodiment, said mesoporous silica is PEGylated. In another embodiment, a tissue-specific targeting agent is bound to the silica shell. In another embodiment, a drug is bound to the silica shell.

In another embodiment, said mesoporous silica is impregnated with a prodrug or drug. In an embodiment, said drug is a chemotherapeutic agent. In an embodiment, said drug is a cytotoxic agent. In an embodiment the metal core dissolves slowly to act as a cytotoxic agent. In an embodiment the drug is selected from the group consisting of mitotic inhibitors, alkylating agents, anti-metabolites, antitumor antibiotics, growth factor inhibitors, cell cycle inhibitors, nzymes, topoisomerase inhibitors, biological response modifiers, anti-hormones, angiogenesis inhibitors, and anti-androgens.

Figure 7:
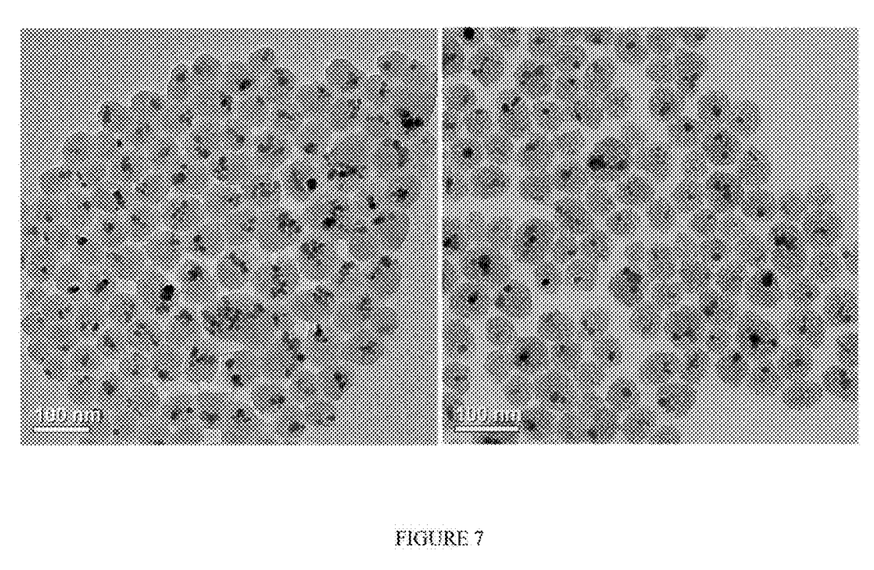
FIG. 7 TEM comparison of morphology of IONPs from Example 1 without (left) and with (right) PVP. The additional PVP helps to stabilize the IONPs before coating, leading to fewer cores per particle. It also helps to localize CTAB near the IONPs, contributing to more centered core/shell structures.
Figure 9:
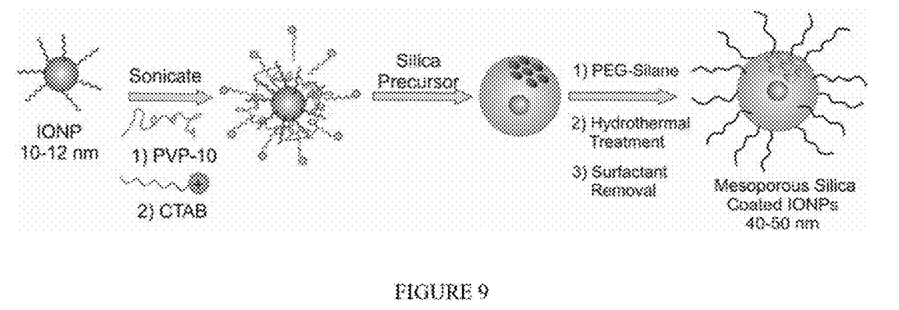
FIG. 9 Illustrates the preparation of representative particles of the invention.

The core/shell particle can be synthesized as illustrated in FIG. 9. Other researchers have coated various IONPs with mesoporous silica previously (Kim, J., et al., *Angew. Chem. Int. Ed.* 2008, 47, 8438-8441; Lin, Y.-S., et al., *Chem. Mater.* 2006, 18, 5170-5172; and Lin, Y.-S., et al., *Chem. Mater.* 2009, 21, 3979-3986); however, the existing surface chemistry of EMG-308 (anionic surfactant) required modifications from the traditional procedure. To ensure effective IONP encapsulation, the silica precursor must condense near the IONP, using it as a 'seed.' (Lin, Y.-S., et al., *Chem. Mater.* 2009, 21, 3979-3986) In traditional syntheses, hydrophobic IONP coatings facilitate this colocalization due to their favorable interaction with the hydrophobic tails of CTAB. The silica precursor preferentially condenses on CTAB scaffolds, resulting in a highly reproducible core/shell structure. With no favorable hydrophobic interactions to anchor CTAB to the IONP, we discovered that an additional layer of a capping agent such as polyvinyl pyrrolidone (PVP, MW 10,000) needed to be used. When sonicated with PVP and CTAB in series, as opposed to simultaneously, prior to silica precursor addition, the IONPs proved stable enough to act as seed sites. FIGS. 2 and 7 compare TEM images of particles that were synthesized with and without PVP. Substantial IONP clumping occurs when PVP is absent. Additionally, the IONPs are more likely to be located at the edges of particles rather than in the center. These observations are probably the result of poor IONP colloidal stability and random seeding of silica precursors.

Figure 4:
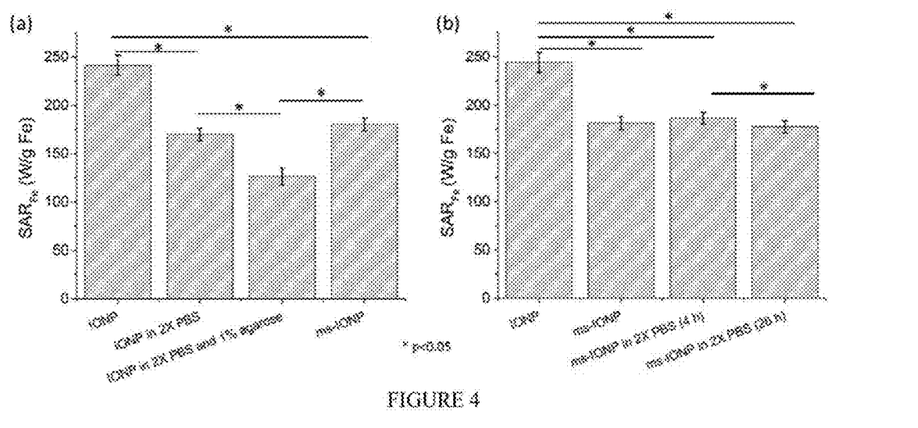
FIG. 4 Characteristics of EMG-308 after coating with mesoporous silica. (a) Heating ability as measured by SAR drops dramatically for uncoated EMG-308 with aggregation from PBS or 1% agarose, but coating keeps the SAR from dropping lower. Additionally, storage of coated IONPs in PBS does not cause substantial changes in SAR over time (b).
Figure 8:
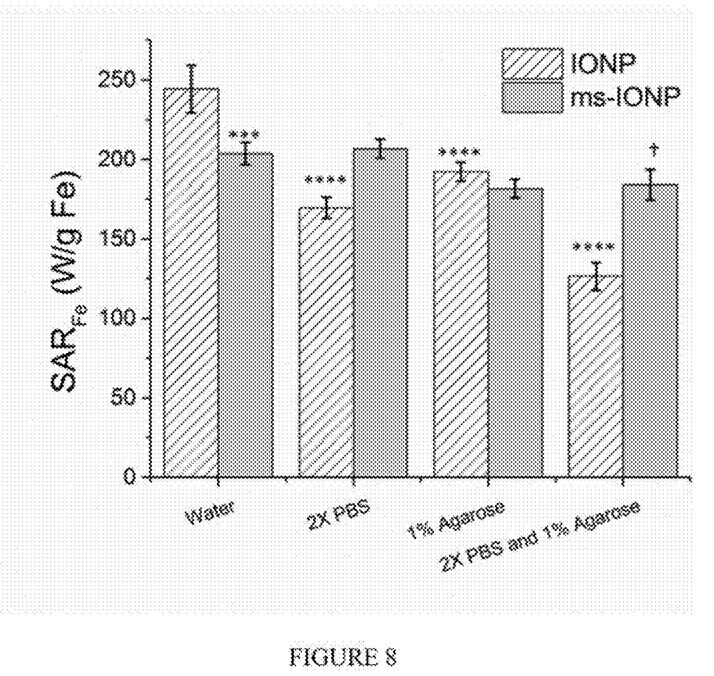
FIG. 8 Characteristics of EMG-308 after coating with mesoporous silica. Heating ability as measured by SAR drops dramatically for uncoated EMG-308 with aggregation from PBS or 1% agarose, but coating keeps the SAR from dropping lower.

The ability of the IONP core to heat and provide MRI contrast following silica condensation was investigated. FIGS. 4 and 8 show that relaxivity values are significantly affected by silica coating. Longitudinal relaxivity undergoes the larger loss, which is to be expected based on the limited access of passing water molecules to the surface of the IONP core. Transverse relaxivity remains high (provided the extra PVP layer is present). The slight drop may be due to some partial oxidation during the synthesis or hydrothermal treatment, although oxygen poor environments are used when possible. In regards to SAR, silica coating results in only a slight loss, indicating that water access does not seem to be a limiting factor in heat dissipation.

Figure 5:
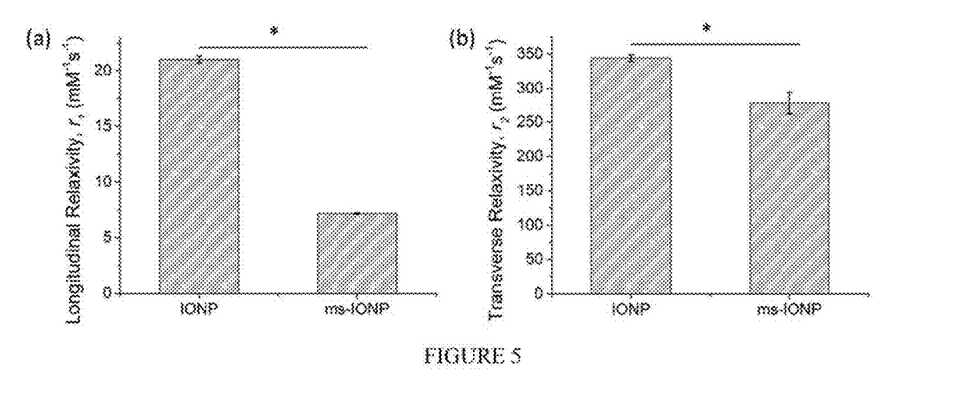
FIG. 5 Longitudinal (a) and transverse (b) relaxivity are affected by mesoporous silica coating. Despite the drops in relaxivity, these particles still display values which compete with standard of care contrast agents (such as gadolinium based).

An unexpected benefit of treating metal oxide cores with a capping agent (e.g. PVP wrapping), prior to exposure to surfactant is apparent in the transverse relaxivity of the particles in that it prevents direct contact between the metal oxide core (e.g. iron oxide core) and the silica shell thereby preventing disruption of the magnetic properties at the surface of the nanoparticle, changing properties such as the longitudinal relaxivity, $r_1$ (Smolensky, E. D., et al., *Chem. Commun.* 2011, 47, 2149). Without the PVP layer, the IONPs from example 1 demonstrate a marked drop in $r_2$, due to direct contact between the IONP and the silica shell (the prolonged hydrothermal treatment and lack of a hydrophobic 'buffer' layer make this scenario likely). Inclusion of excess PVP leads to recovery of $r_1$ (FIG. 5)

Accordingly, in another aspect of the invention, there is provided a process for making a mesoporous silica coated metal oxide nanoparticle comprising:
  i. providing a metal oxide nanoparticle core;
  ii. coating said core with a capping agent;
  iii. contacting the coated nanoparticle with a cationic surfactant; and
  iv. encapsulating said nanoparticle from step (iii) with mesoporous silica shell. In an embodiment, the process further comprises hydrothermally treating the nanoparticle from step (iv).

In an embodiment, the capping agent is mixed with the metal oxide core in a concentration from at least about 5 mM. In an embodiment, the capping agent is mixed with the metal oxide core in a concentration from at least about 8 mM. In an embodiment, the capping agent is mixed with the metal oxide core in a concentration from at least about 10 mM. In an embodiment, the capping agent is mixed with the metal oxide core in a concentration from at least about 12 mM. In an embodiment, the capping agent is mixed with the metal oxide core in a concentration from at least about 20 mM.

During synthesis, the metal oxide core/capping agent mixture can be measured by dynamic light scattering (DLS) and compared to the hydrodynamic diameter immediately before coating with a capping agent addition. The diameter scales in accordance with the amount of capping agent (e.g. PVP). In an embodiment, the average hydrodynamic diameter of the nanoparticle is about 1% to about 20% greater after coated with capping agent. In an embodiment, the average hydrodynamic diameter of the nanoparticle is about 5% to about 10% greater after coated with capping agent.

In an embodiment, there are about 100,000 capping molecules attached to each nanoparticle core. In an embodiment, there are about 250,000 capping molecules attached to each nanoparticle core. In an embodiment, there are about 500,000 capping molecules attached to each nanoparticle core. In an embodiment, there are about 750,000 capping molecules attached to each nanoparticle core. In an embodiment, there are about 1,000,000 capping molecules attached to each nanoparticle core. In an embodiment, there are about 1,250,000 capping molecules attached to each nanoparticle core. In an embodiment, there are about 1,500,000 capping molecules attached to each nanoparticle core. In an embodiment, there are about 2,000,000 capping molecules attached to each nanoparticle core. In a particular embodiment, the capping agent is PVP-10.

In an embodiment, said metal oxide core is coated with an anionic surfactant prior to coating with a capping agent. In an embodiment, said metal oxide core is iron-oxide. In an embodiment, said cationic surfactant is CTAB, CTAC (cetyl trimethylammonium chloride), and decylamine. In an embodiment, said cationic surfactant is CTAB.

In an embodiment, said nanoparticle from step (iv) is hydrothermally treated until the substantially greater abundance of fully condensed silane relative to mono- and di-hydroxy forms.

Diagnostic Methods:

In another aspect of the invention there is provided a method of diagnostic imaging comprising administering to a mammal, a mesoporous silica coated nanoparticle of the invention and detecting said nanoparticle in the mammal. In an embodiment, the nanoparticle of the invention is detected using magnetic resonance imaging (MRI).

Methods of Use:

Nanotechnology has the potential to revolutionize medical diagnosis and treatment with magnetic nanoparticles emerging at the forefront of the field. These systems enable the localized delivery of thermal energy, which can induce cell death in malignant tumors sensitive to a moderate temperature increase or stimulate the release of drug from temperature-sensitive carriers. This approach overcomes some drawbacks of currently available therapies by exposing only the diseased region to activated particles. For such applications, nanoparticles of the invention would ideally work in a designed, narrow temperature range and thereby would have minimal toxicity on normal cells.

The methods further include controlling the nanoparticles by a magnetically heating process to release those molecules regularly where the magnetic field generator could be external or internal the human bodies.

In an embodiment, a method includes magnetically heating adjacent material with the nanoparticles of the invention. The method further includes maintaining a predetermined temperature based on a magnetic property of the nanoparticles. In an embodiment, magnetization of the nanoparticles substantially decreases when a temperature of the nanoparticles reaches a predetermined value. In an embodiment, the nanoparticles cease heating up when a temperature of the nanoparticles reaches a predetermined value. In an embodiment, heating the nanoparticles includes heating the nanoparticles to a temperature 60° C.-100° C. suitable for ablations, or heating the nanoparticles to a temperature between 40° C. to 60° C. suitable for magnetic hyperthermia. The heating power, in an option, is sensitive to an exchange coupling constant between magnetic atoms in the nanoparticles, or a magnetocrystalline anisotropy constant of the nanoparticle.

In an aspect of the invention, mesoporous silica-coated nanoparticles of the invention are administered to a mammal and heated by subjecting them to an alternating magnetic field. In an embodiment, there is provided a method of treating a tumor in a mammal comprising administering nanoparticles of the invention to said mammal and heating said nanoparticles by subjecting them to an alternating magnetic field. In an embodiment, the nanoparticles are administered directly into said tumor. In another embodiment, the nanoparticles accumulate at the site of the tumor or in the tumor cells after intravenous injection.

In another aspect, there is provided a method of treating a disease or disorder comprising administering to a mammal a nanoparticle of the invention in which said nanoparticle has bound thereto a drug for treating said disease or disorder. In another embodiment, there is provided a method of treating a disease or disorder by administering to a mammal a nanoparticle of the invention in which the silica shell is impregnated with a drug for treating said disease or disorder.

Pharmaceutical Compositions: In another aspect of the invention there is provided pharmaceutical compositions comprising mesoporous silica coated nanoparticles of the invention and a pharmaceutically acceptable carrier, excipient or diluent. In an embodiment, the composition may be in any suitable form such as a solution, a suspension, an emulsion, an infusion device, or a delivery device for implantation or it may be presented as a dry powder to be reconstituted with water or another suitable vehicle before use. The composition may include suitable parenterally acceptable carriers and/or excipients.

In an embodiment, the compositions may be in a form suitable for administration by sterile injection. To prepare such a composition, the nanoparticles of the invention are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). For parenteral formulations, the carrier will usually comprise sterile water, though other ingredients, for example, ingredients that aid solubility or for preservation, may be included. Injectable solutions may also be prepared in which case appropriate stabilizing agents may be employed.

Formulations suitable for parenteral administration usually comprise a sterile aqueous preparation, which may be, for example, isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intratumoral, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

EXAMPLES

Chemicals: Tetraethylortho silicate (TEOS), n-cetyltrimethylammonium bromide (CTAB), and polyvinylpyrrolidone (PVP-10, average molecular weight 10,000) were purchased from Sigma Aldrich (Milwaukee, Wis.). 2-[methoxy(polyethyleneoxy)-propyl]9-12-trimethoxysilane (PEG-silane, molecular weight 596-725 g/mol, 9-12 EO) was obtained from Gelest, Inc. (Morrisville, Pa.). Chlorotrimethylsilane (TMS, >99%) was purchased from Fluka. Ethanol (95 and 99%) were purchased from Pharmco-Aaaper (Brookfield, Conn.). EMG-308 Ferrofluid was purchased from Ferrotec (Santa Clara, Calif.). Ammonium hydroxide ($NH_4OH$, 28%) was obtained from Avantor Performance Materials. Ammonium Nitrate ($NH_4NO_3$) was purchased from Mallinckrodt Chemicals (Phillipsburg, N.J.). Phosphate buffered saline (PBS, 10×) was obtained from Life Technologies. Fetal bovine serum (FBS, 100%) was purchased from Hyclone (Logan, Utah). Ultra-pure water was generated using a Millipore Milli-Q water purification system (Billerica, Mass.).

Example 1 Synthesis and Purification

Synthesis of core/shell nanoparticles was modified from our previous procedures (CITE). First, 0.6 g PVP-10 were added to 5 mL MQ $H_2O$ and dissolved with sonication (bath sonicator, Branson 2510). While sonicating, 400 μL of stock EMG-308 was added to the solution. The suspension was sonicated intensely for 1 h, and then 0.29 g of CTAB were added. The suspension was sonicated for an additional 30-60 min. Next, 150 g of ultrapure water were added to a 250 mL Erlenmeyer flask which was then placed in the sonicator. While sonicating, the iron-containing suspension was slowly pipetted into the aqueous solution, allowing ample time for individual droplets to disperse. The resulting rusty orange suspension was covered with parafilm and allowed to sonicate for 1 hour. The flask was then placed in an oil bath at 50° C. and the suspension was stirred at 700 rpm for about 15 minutes to allow temperature equilibration. The parafilm was removed from the flask and 2.5 mL 28% $NH_4OH$ was added to make the synthetic solution basic. After 5 minutes, 2.5 mL of 0.88 M ethanolic TEOS were added dropwise. The suspension was stirred at 700 rpm for 1 hour before adding 450 μL PEG-silane. After an additional 30 minutes of stirring, 68 µL of TMS were added. The suspension was allowed to stir for 30 minutes, then transferred to a 250 mL beaker without a stir bar and allowed to age at 50° C. for 20 hours. This aging period allows silica condensation and water evaporation for easier suspension workup.

All samples underwent deoxygenated hydrothermal treatment as described in our previous work (Hurley, K. R., et al., Chem. Mater. 2013, 25, 1968-1978). Samples were sparged with nitrogen gas for 15 minutes and then vacuum sonicated to remove the majority of the oxygen in the system. The headspace of each sample container was filled with nitrogen prior to treatment in a drying oven at 90° C.

Following hydrothermal treatment, samples were purified via a series of centrifugation steps as described in our previous work (Lin, Y.-S., et al., J. Am. Chem. Soc. 2011, 133, 20444-20457; and Hurley, K. R., et al., Chem. Mater. 2013, 25, 1968-1978). The suspension was centrifuged at 66226×g for 30 minutes and redispersed in 50 mL of 6 g/L ethanolic $NH_4NO_3$. The $NH_4NO_3$ suspension was stirred at 300 rpm and 60° C. for 1 hour to assist in the removal of excess CTAB surfactant. The sample was centrifuged again at 66226×g for 20 minutes and redispersed in 95% ethanol. The $NH_4NO_3$ step was repeated, followed by centrifugation and redispersal in 95% ethanol. The samples were centrifuged and redispersed in 99% ethanol twice more to complete the purification process.

Example 2 Materials Characterization

Dynamic light scattering and zeta potential measurements were performed on a Brookhaven Zeta PALS instrument with a 635 nm red diode laser with 15 mW of power. Samples were run in materials triplicates and results are reported as the average of three instrumental 1-minute runs.

Transmission electron microscopy was performed on a Tecnai T12 transmission electron microscope operating at 120 kV. Nanoparticle samples were deposited on a 200 mesh copper TEM grid with carbon and formvar supports (Ted Pella, Inc.) by briefly dipping the grid into an ethanolic suspension of nanoparticles and allowing the grid to air dry. Cell and tissue samples were embedded into resin via a typical process of fixation, staining, dehydration, epoxy infiltration, and curing.

Powder x-ray diffraction was primarily performed on a Siemens D5005 instrument with a copper source. Data was collected with a step size of 0.18 degrees 2θ and a dwell time of 1 s.

Nitrogen physisorption measurements were performed on a Micromeritics ASAP 2020 instrument. Samples were powdered by evaporation of ethanol suspensions and finely ground with a spatula. Before physisorption measurements, samples were degassed at 120° C. for 8 h. BET theory was used to calculate surface area, and BJH/KJS methods were used to calculate pore volume and pore diameter.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the invention should, therefore, be determined with reference to the appended claims, along with the full scope of equivalents to which such claims are entitled. All publications, patents, and patent documents are incorporated by reference herein, as though individually incorporated by reference.

What is claimed is:

1. A mesoporous silica coated metal oxide nanoparticle comprising:
    a metal oxide nanoparticle core;
    a layer of a capping agent encompassing a surface of said metal oxide nanoparticle core wherein the capping agent is PVP, PAA (polyacrylamide), PAH (polyalkylamine hydrochloride), PEI (polyethyleneimine) or dextran; and
    a mesoporous silica shell encapsulating the metal oxide core;
    wherein the mesoporous silica shell and the metal oxide core are not in full contact; and wherein the longitudinal relaxivity of the mesoporous silica coated metal oxide nanoparticle is at least 20% of the longitudinal relaxivity of the corresponding metal oxide nanoparticle; and
    wherein the mesoporous silica coated metal oxide nanoparticle is prepared by:
    (i) coating the metal oxide nanoparticle core with a capping agent to provide a capped nanoparticle core;
    ii) contacting the capped nanoparticle core from step (i) with a cationic surfactant to provide a resulting nanoparticle; and
    (iii) encapsulating the resulting nanoparticle from step (ii) with a mesoporous silica shell.

2. A mesoporous silica coated metal oxide nanoparticle comprising:
    a metal oxide nanoparticle core;
    a layer of a capping agent encompassing a surface of said metal oxide nanoparticle core; wherein the capping agent is PVP, PAA (polyacrylamide), PAH (polyalkylamine hydrochloride), PEI (polyethyleneimine) or dextran; and
    a mesoporous silica shell encapsulating the metal oxide core;
    wherein the mesoporous silica shell and the metal oxide core are not in direct contact;
    wherein the longitudinal relaxivity of the mesoporous silica coated metal oxide nanoparticle is at least 20% of the longitudinal relaxivity of the corresponding metal oxide nanoparticle; and
    wherein the mesoporous silica coated metal oxide nanoparticle is prepared by:
    (i) coating the metal oxide nanoparticle core with a capping agent to provide a capped nanoparticle core;
    ii) contacting the capped nanoparticle core from step (i) with a cationic surfactant to provide a resulting nanoparticle; and
    (iii) encapsulating the resulting nanoparticle from step (ii) with a mesoporous silica shell.

3. The nanoparticle of claim 2, wherein the core is iron-oxide.

4. The nanoparticle of claim 2, wherein the capping agent is PVP.

5. The nanoparticle of claim 2, wherein the average hydrodynamic diameter of the metal oxide nanoparticle core having a surface encompassed with a layer of a capping agent is about 1% to about 20% greater than the hydrodynamic diameter of the corresponding metal oxide nanoparticle core.

6. The nanoparticle of claim 2, wherein the average hydrodynamic diameter of the metal oxide nanoparticle core having a surfaced encompassed with a layer of a capping agent is about 5% to about 10% greater than the hydrodynamic diameter of the corresponding metal oxide nanoparticle core.

7. The nanoparticle of claim 1, wherein the silica shell is impregnated with a drug.

8. The nanoparticle of claim 7, wherein the drug is a chemotherapeutic agent.

9. The nanoparticle of claim 1, further comprising a drug bound to the silica shell.

10. The nanoparticle of claim 1, further comprising a targeting agent bound to the silica shell.

11. The nanoparticle of claim 2, wherein the average distance between the metal core and the silica shell is about 0.1 nm to about 5 nm.

12. The nanoparticle of claim 2, wherein the average distance between the metal core and the silica shell is about 0.5 nm to about 3 nm.

13. The nanoparticle of claim 1, wherein the core is iron-oxide.

14. The nanoparticle of claim 1, wherein the capping agent is PVP.

15. The nanoparticle of claim 1, wherein the average hydrodynamic diameter of the metal oxide nanoparticle core having a surface encompassed with a layer of a capping agent is about 1% to about 20% greater than the hydrodynamic diameter of the corresponding metal oxide nanoparticle core.

16. The nanoparticle of claim 1, wherein the average hydrodynamic diameter of the metal oxide nanoparticle core having a surfaced encompassed with a layer of a capping agent is about 5% to about 10% greater than the hydrodynamic diameter of the corresponding metal oxide nanoparticle core.

17. The nanoparticle of claim 1, wherein the average distance between the metal core and the silica shell is about 0.1 nm to about 5 nm.

18. The nanoparticle of claim 1, wherein the average distance between the metal core and the silica shell is about 0.5 nm to about 3 nm.

19. The nanoparticle of claim 1, wherein the cationic surfactant is CTAB.

20. The nanoparticle of claim 2, wherein the cationic surfactant is CTAB.

21. A process for making a mesoporous silica coated metal oxide nanoparticle comprising:
a metal oxide nanoparticle core;
a layer of a capping agent encompassing a surface of said metal oxide nanoparticle core wherein the capping agent is PVP, PAA (polyacrylamide), PAH (polyalkylamine hydrochloride), PEI (polyethyleneimine) or dextran; and
a mesoporous silica shell encapsulating the metal oxide core;
wherein the mesoporous silica shell and the metal oxide core are not in direct contact and wherein the longitudinal relaxivity of the mesoporous silica coated metal oxide nanoparticle is at least 20% of the longitudinal relaxivity of the corresponding metal oxide nanoparticle;
comprising the steps of:
  i. providing a metal oxide nanoparticle core;
  ii. coating said core with a capping agent to provide a capped nanoparticle core;
  iii. contacting the capped nanoparticle core from step (ii) with a cationic surfactant to provide a resulting nanoparticle; and
  iv. encapsulating the resulting nanoparticle from step (iii) with mesoporous silica shell.

22. The process of claim 21, further comprising hydrothermally treating the nanoparticle from step (iv).

23. The process of 21, wherein the metal oxide core is iron-oxide.

24. The process of 21, wherein the capping agent is PVP-10.

25. The process of 21, wherein the cationic surfactant is CTAB.

26. A method of treating a disease or disorder by administering to a mammal a nanoparticle according to claim 1, wherein the silica shell is impregnated with or bound to a drug that is effective treating said disease or disorder.

27. The method of claim 26, wherein the nanoparticle core is iron-oxide.

28. The method of claim 26, wherein the capping agent is PVP.

29. The method of claim 26, wherein said disease or disorder is a cancer.

30. The method of claim 26, wherein said drug is a chemotherapeutic agent.

31. The method of claim 26, wherein said drug is selected from the group consisting of mitotic inhibitors, alkylating agents, anti-metabolites, antitumor antibiotics, growth factor inhibitors, cell cycle inhibitors, enzymes, topoisomerase inhibitors, biological response modifiers, anti-hormones, angiogenesis inhibitors, and anti-androgens.

* * * * *